US010488639B2

(12) United States Patent
Chang et al.

(10) Patent No.: US 10,488,639 B2
(45) Date of Patent: Nov. 26, 2019

(54) DETECTION DEVICE FOR SPECIMENS

(71) Applicant: VisEra Technologies Company Limited, Hsin-Chu (TW)

(72) Inventors: Chin-Ching Chang, Hsinchu (TW); Han-Lin Wu, Hsin-Chu (TW); Chin-Chuan Hsieh, Hsin-Chu (TW); Wei-Ko Wang, Taoyuan (TW); Zong-Ru Tu, Keelung (TW)

(73) Assignee: Visera Technologies Company Limited, Hsin-Chu (TW)

( * ) Notice: Subject to any disclaimer, the term of this patent is extended or adjusted under 35 U.S.C. 154(b) by 215 days.

(21) Appl. No.: 14/878,272

(22) Filed: Oct. 8, 2015

(65) Prior Publication Data

US 2017/0102530 A1   Apr. 13, 2017

(51) Int. Cl.
*G02B 21/00*   (2006.01)
*G01N 21/64*   (2006.01)
(Continued)

(52) U.S. Cl.
CPC ..... *G02B 21/0008* (2013.01); *G01N 21/6452* (2013.01); *G01N 21/6486* (2013.01);
(Continued)

(58) Field of Classification Search
CPC .. G02B 21/0008; G02B 21/06; G02B 21/361; G01N 21/6452; G01N 21/6486;
(Continued)

(56) References Cited

U.S. PATENT DOCUMENTS 6,580,081 B1 *   6/2003   Thorwirth .......... G01N 21/6428
                                                         250/458.1
6,959,138 B2 *   10/2005  Steenblik ......... B29D 11/00663
                                                         385/129
(Continued)

FOREIGN PATENT DOCUMENTS

CN          1455002 A      11/2003
CN          1819286 A       8/2006
(Continued)

OTHER PUBLICATIONS

Buehlmann P. et al. In-situ silicon oxide based intrmediate reflector for thin-film silicon micromorph solar cells, Appl. Phys. Lett. 91 143505 (2007).*
(Continued)

*Primary Examiner* — Richard A Hansell, Jr.
(74) *Attorney, Agent, or Firm* — Muncy, Geissler, Olds & Lowe, P.C.

(57) ABSTRACT

A detection device for specimens includes an image sensor, a light-guiding structure, and a carrier. The image sensor includes a sensing area and a non-sensing area around the sensing area. The light-guiding structure is disposed on the image sensor. The light-guiding structure includes a central guiding portion, a reflection layer, and first guiding portions. The central guiding portion is located over the sensing area. The reflection layer is disposed on the image sensor and includes channels located over the non-sensing area. The first guiding portions are located in the channels, and connected to the central guiding portion and a side surface of the light-guiding structure. The carrier is disposed on the light-guiding structure, and has wells located over the sensing area. Each of the wells is configured to receive a specimen.

16 Claims, 12 Drawing Sheets

(51) Int. Cl.
*G02B 21/06* (2006.01)
*G02B 21/36* (2006.01)

(52) U.S. Cl.
CPC ........... *G02B 21/06* (2013.01); *G02B 21/361* (2013.01); *G01N 21/6454* (2013.01); *G01N 2021/6471* (2013.01); *G01N 2021/6478* (2013.01); *G01N 2201/0461* (2013.01); *G01N 2201/062* (2013.01); *G01N 2201/068* (2013.01); *G01N 2201/06113* (2013.01); *G01N 2201/0873* (2013.01)

(58) Field of Classification Search
CPC ......... G01N 21/6454; G01N 2201/068; G01N 2201/0461; G01N 2021/6478; G01N 2021/6471; G01N 2201/0873; G01N 2201/062; G01N 2201/06113
USPC ........................................................ 348/79
See application file for complete search history.

(56) References Cited

U.S. PATENT DOCUMENTS

| | | | | |
|---|---|---|---|---|
| 9,812,597 | B2* | 11/2017 | Yu | B82Y 20/00 |
| 2004/0052488 | A1* | 3/2004 | Bierhoff | G02B 6/10 |
| | | | | 385/129 |
| 2005/0084229 | A1* | 4/2005 | Babbitt | G02B 6/0003 |
| | | | | 385/146 |
| 2009/0311774 | A1* | 12/2009 | Chiou | B82Y 30/00 |
| | | | | 435/288.7 |
| 2010/0025567 | A1* | 2/2010 | Lueerssen | G02B 21/245 |
| | | | | 250/205 |
| 2010/0096561 | A1* | 4/2010 | Johnson | G01N 21/6428 |
| | | | | 250/459.1 |
| 2010/0171717 | A1* | 7/2010 | Hu | G06F 3/0386 |
| | | | | 345/173 |
| 2011/0018801 | A1* | 1/2011 | Wang | G02F 1/133512 |
| | | | | 345/158 |
| 2011/0198717 | A1* | 8/2011 | Lee | H01L 27/14636 |
| | | | | 257/437 |
| 2011/0223590 | A1* | 9/2011 | Chiou | C12Q 1/6869 |
| | | | | 435/6.1 |
| 2011/0306143 | A1* | 12/2011 | Chiou | B82Y 15/00 |
| | | | | 436/94 |
| 2013/0143206 | A1* | 6/2013 | McCaffrey | C12Q 1/6869 |
| | | | | 435/6.1 |
| 2014/0268864 | A1* | 9/2014 | Lee | G02B 6/0008 |
| | | | | 362/558 |
| 2016/0020353 | A1* | 1/2016 | Chu | H01L 31/02327 |
| | | | | 257/21 |
| 2016/0038759 | A1* | 2/2016 | Andersen | A61N 1/0551 |
| | | | | 607/88 |

FOREIGN PATENT DOCUMENTS

| | | | |
|---|---|---|---|
| CN | 101523198 | A | 9/2009 |
| CN | 102713572 | A | 10/2012 |
| CN | 103946690 | A | 7/2014 |
| CN | 104620113 | A | 5/2015 |
| TW | M493674 | U | 1/2015 |
| TW | 201505441 | A | 2/2015 |
| TW | I497705 | B | 8/2015 |
| WO | WO 2014137097 | A2 | 9/2014 |
| WO | WO-2014207089 | A1 * | 12/2014 ......... G01N 21/6458 |

OTHER PUBLICATIONS

Buehlmann P. et al. In-situ silicon oxide based intrmediate reflector for thin-film silicon micromorph solar cells, Appl. Phys. Lett.91 143505 (2007). (Year: 2007).*
Taiwanese Office Action dated Dec. 7, 2016 from corresponding Applilcation No. 105105088; 5 pgs.
Chinese Patent Office. Office Action, dated Nov. 16, 2018. 5 pages.
Chinese Patent Office. Office Action Search Report, dated Nov. 16, 2018. 3 pages.

* cited by examiner

DETECTION DEVICE FOR SPECIMENS

BACKGROUND OF THE INVENTION

Field of the Invention

The present disclosure relates to a detection device, and in particular to a detection device for specimens.

Description of the Related Art

Various biochips, such as microfluidic chips, micro-array chips, or lab-on-a-chips, have been developed to detect the human genome, and thus research into sequencing the human genome has been greatly improved. A person's blood can be analyzed to check whether the blood contains a biomarker for a specific disease. That is how genetic diseases can be detected.

FIG. 1 is a schematic diagram of a conventional biochip detection device A1. The biochip detection device A1 is used for detecting specimens A2 carried on a biochip A3. The biochip A3 includes a number of wells A31 arranged in an array for receiving the specimens A2. The biochip detection device A1 includes a laser source A10, a filter A20, a beam splitter A30, a lens A40, a filter A50, a lens A60 and a detector A70.

The laser source A10 emits an excitation beam L1 toward the beam splitter A30. The filter A20 is located between the laser source A10 and the beam splitter A30 and is used for filtering the excitation beam L1 with a desired wavelength. For example, the wavelength of the excitation beam L1 is in a range from about 210 nm to 300 nm after passing the filter A20. The beam splitter A30 reflects the excitation beam L1 to the specimen A2. The lens A40 focuses the excitation beam L1 on the specimen A2.

After the specimen A2 is irradiated by the excitation beam L1, the specimen emits an induced beam L2 to the filter A50 by passing through the beam splitter A30. In general, the induced beam L2 is a fluorescence beam. The filter A50 is for blocking the excitation beam L1, since a portion of the excitation beam L1 may pass through the beam splitter A30 to the detector A70.

The lens A60 is for focusing the induced beam L2 on the detector A70. The detector A70 is for analyzing the wavelength and the strength of the induced beam L2. However, since the excitation beam L1 and the induced beam L2 have the same optical path, the induced beam L2 detected by the detector A70 is distributed by the excitation beam L1. Therefore, thus the detection result of the specimen A2 is influenced.

The conventional biochip detection device A1 detects the specimen A2 in a point-by-point manner, thus it will be very time-consuming whenever it scans a biochip A3 with numerous specimens A2.

Moreover, as shown in FIG. 1, the conventional biochip detection device A1 includes a large amount of optical elements, and a transport device is also needed to move the biochip detection device A1 for detecting the specimens A2 in sequence. Therefore, the size and the weight of the biochip detection device A1 is great, and the manufacturing cost of the biochip detection device A1 is expensive. The biochip detection device A1 is not portable or affordable for users.

Although biochip detection devices have been generally adequate for their intended purposes, they have not been entirely satisfactory in all respects. Consequently, it is desirable to provide a solution for improving biochip detection devices.

BRIEF SUMMARY OF THE INVENTION

The present disclosure provides a detection device with a small size and a light weight for portability. Moreover, the manufacturing cost of the detection device is decreased, and the time required for detection of the specimens is also decreased.

The present disclosure provides a detection device for specimens, including an image sensor, a light-guiding structure, and a carrier. The image sensor includes a sensing area and a non-sensing area around the sensing area. The light-guiding structure is disposed on the image sensor. The light-guiding structure includes a central guiding portion, a reflection layer, and a number of first guiding portions.

The central guiding portion is located over the sensing area. The reflection layer is disposed on the image sensor, and includes a number of channels located over the non-sensing area. The first guiding portions are located in the channels, and connected to the central guiding portion and a side surface of the light-guiding structure. The carrier is disposed on the light-guiding structure, and has a number of wells arranged in an arrangement array located over the sensing area. Each of the wells is configured to receive a specimen.

In conclusion, since the detection device is integrated with the image sensor and the light-guiding structure, the size and the weight of the detection device are greatly decreased, and the manufacturing cost of the detection device is cheap. By the light-guiding structure, the light emitting efficiency of the light sources is improved. Moreover, the specimens on the carrier can be detected by the image sensor at the same time, and the thus the time required for detection of the specimens is decreased.

BRIEF DESCRIPTION OF THE DRAWINGS

The invention can be more fully understood by reading the subsequent detailed description and examples with references made to the accompanying drawings, wherein.

DETAILED DESCRIPTION OF THE INVENTION

Figure 1:
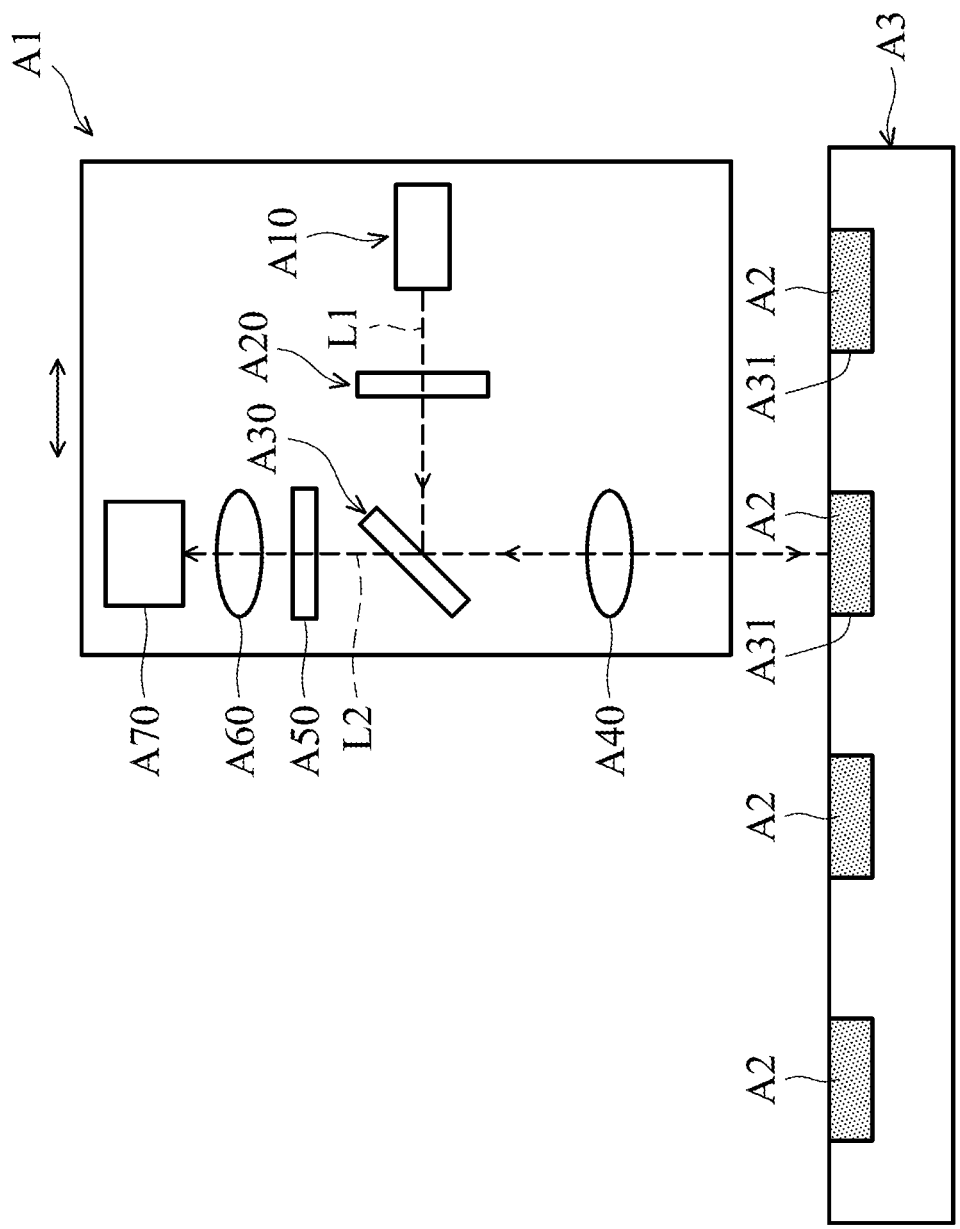
FIG. 1 is a schematic diagram of a conventional biochip detection device.

The following disclosure provides many different embodiments, or examples, for implementing different features of the present disclosure. Specific examples of components and arrangements are described below to simplify the present disclosure. For example, the formation of a first feature over or on a second feature in the description that follows may include embodiments in which the first and second features are formed in direct contact, and may also include embodiments in which additional features may be formed between the first and second features, such that the first and second features may not be in direct contact.

In addition, the present disclosure may repeat reference numerals and/or letters in the various examples. This repetition is for the purpose of simplicity and clarity and does not in itself dictate a relationship between the various embodiments and/or configurations discussed. Furthermore, the shape, size, and thickness in the drawings may not be drawn to scale or simplified for clarity of discussion; rather, these drawings are merely intended for illustration.

Figure 2:
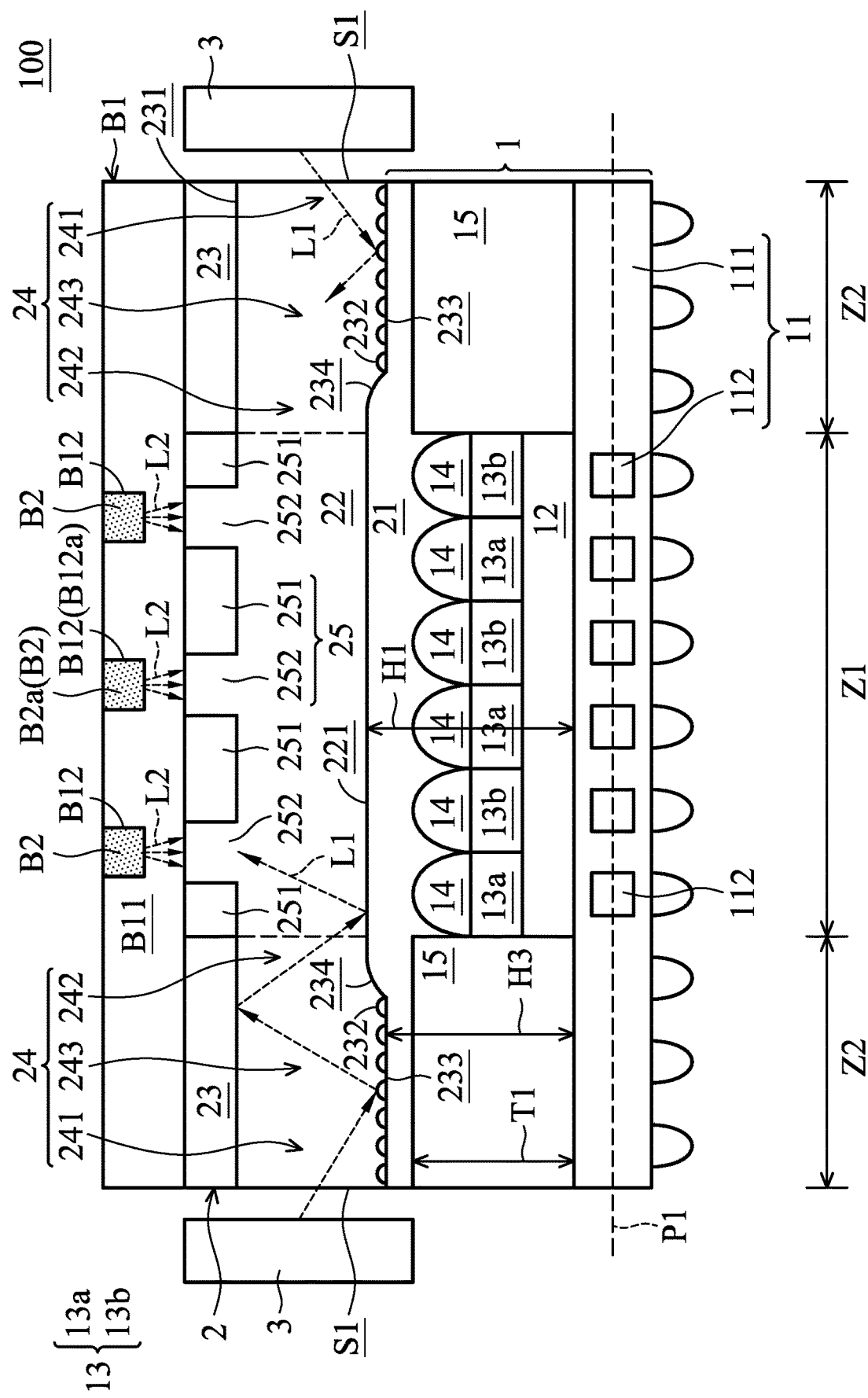
FIG. 2 is a schematic view of a detection device in accordance with some embodiments of the present disclosure.
Figure 3:
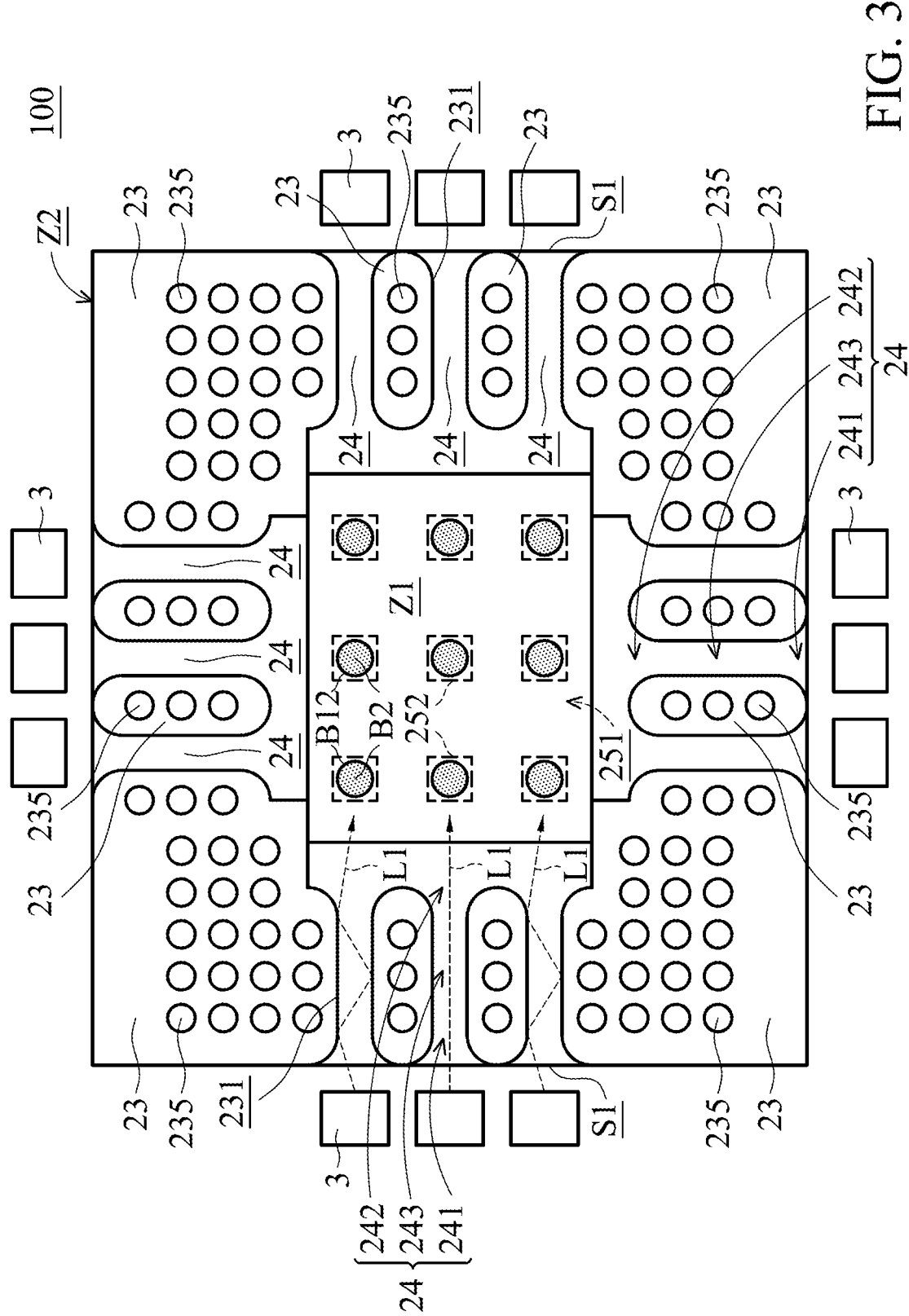
FIG. 3 is a top view of the detection device in accordance with some embodiment of the present disclosure.

FIG. 2 is a schematic view of a detection device 100 in accordance with some embodiments of the present disclosure. FIG. 3 is a top view of the detection device 100 in accordance with some embodiment of the present disclosure. The detection device 100 includes an image sensor 1, a light-guiding structure 2, and light sources 3. The light-guiding structure 2 is disposed on the image sensor 1, and the light sources 3 are adjacent to side surfaces S1 of the light-guiding structure 2. A carrier B1 is disposed on the light-guiding structure 2, and configured to contain a specimen B2.

The light sources 3 are configured to emit excitation beams L1 to the light-guiding structure 2. In some embodiments, the light sources 3 are laser sources, or LEDs (Light-Emitting Diodes). The wavelength of the excitation beam L1 is in a range from about 21 nm to 210 nm. In other words, the excitation beam L1 is a blue light beam or an ultraviolet light beam.

The light-guiding structure 2 is configured to transmit and guide the excitation beam L1 to the specimen B2. When the specimens B2 are irradiated by the excitation beam L1, the specimens B2 emit induced beams L2 to the image sensor 1. In some embodiments, the induced beams L2 are fluorescence beams. The image sensor 1 is configured to sense the induced beams L2 and generate detection signals according to the induced beams L2 falling on the image sensor 1.

The image sensor 1 may be a CMOS (Complementary Metal-Oxide-Semiconductor) image sensor 1, a CCD (charge-coupled device) image sensor 1, or a SPAD (single-photon avalanche diode) image sensor 1. The image sensor 1 is manufactured by a semiconductor manufacturing process.

The image sensor 1 is a plate structure, and includes a sensing layer 11, a cutting layer 12, a number of filter units 13, a number of microlenses 14, and a shielding portion 15. The sensing layer 11 extends along a reference plane P1. The sensing layer 11 is configured to sense the induced beams L2 and generate detection signals according to the induced beams L2 falling on the sensing layer 11.

The sensing layer 11 may include all of the following elements, but the sensing layer 11 does not necessarily need to include all of the following elements since the objective of the sensing layer 11 is achieved. The sensing layer 11 includes a substrate 111 and a number of sensing units 112. In some embodiments, the sensing layer 11 further includes other optional layers (not shown in figures).

The sensing units 112 are disposed in the substrate 111. The sensing units 112 are arranged in a sensing array at the reference plane P1. In some embodiments, the sensing units 112 are photodiodes. Each of the sensing units 112 is configured to sense the induced beam L2 and generate a detection signal according to the induced beam L2 falling thereon.

In the embodiments, the image sensor 1 includes a sensing area Z1 and a non-sensing area Z2 around the sensing area Z1. In other words, the sensing area Z1 is a central area of the image sensor 1, and the non-sensing area Z2 is an edge area of the image sensor 1. The sensing units 112 are located in the sensing area Z1. In some embodiments, the sensing units 112 are not located in the non-sensing area Z2. In some embodiments, the sensing area Z1 is about 0.2 times to 4 times the non-sensing area Z2.

The cutting layer 12 is disposed between the sensing layer 11 and the microlenses 14. In some embodiments, the cutting layer 12 is disposed between the sensing layer 11 and the filter units 13. The cutting layer 12 is configured to block the excitation beam L1 passing through to the sensing layer 11.

The filter units 13 are disposed on the sensing layer 11, and located in the sensing area Z1. In some embodiments, the filter units 13 are not located in the non-sensing area Z2. The filter units 13 are arranged in a filter array at a plane parallel to the reference plane P1. Each of the filter units 13 is located over one of the sensing units 112.

Each of the filter units 13 allows a predetermined range of wavelengths of light to pass. In some embodiments, the filter units 13 are color filter units. For example, the filter units 13 include a number of red filter units 13a and a number of yellow filter units 13b. The red filter units 13a and the yellow filter units 13b are arranged alternately in an array.

The red filter units 13a allow wavelengths of induced beam L2 in a range from 620 nm to 750 nm (red light) to pass to the sensing unit 12 under the red filter units 13a. The yellow filter units 13b allow wavelengths of induced beam L2 in a range from 590 nm to 620 nm (yellow light) to pass to the sensing unit 12 under the yellow filter units 13b.

The microlenses 14 are disposed on the filter units 13 and arranged in a microlens array at a plane parallel to the reference plane P1. The microlenses 14 are located in the sensing area Z1. In some embodiments, the microlenses 14 are not located in the non-sensing area Z2. Each of the microlenses 14 is located over one of the filter units 13. The microlenses 14 are configured to focus the light (induced beams L2) to the sensing units 112. The microlenses 14 are also configured to reflect the excitation beam L1 toward the wells B12 via the second guiding portions 252.

The shielding portion 15 is disposed in the non-sensing area Z2, around the cutting layer 12, the filter units 13 and the microlenses 14. The shielding portion 15 is configured to prevent the excitation beams L1 to pass to the filter units 13 and the microlenses 14 directly from the light sources 3.

In some embodiments, the thickness T1 of the shielding portion 15 is equal to or greater than the height of the top of the microlenses 14 relative to the sensing layer 11. The color of the shielding portion 15 is black. A transmittance of the shielding portion 15 is less than 30%.

The carrier B1 may be a biochip, such as a microfluidic chip, a micro-array chip, or a lab-on-a-chip. In this embodiment, the carrier B1 is a micro-array chip. In some embodiments, the carrier B1 is detachably disposed on the light-guiding structure 2. In some embodiments, the carrier B1 is fixed at and integrated with the light-guiding structure 2.

The carrier B1 is a plate structure, extending parallel to the reference plane P1. The carrier B1 includes a carrying body B11 and a number of wells B12 formed on the top surface of the carrying body B11. The wells B12 are arranged in an arrangement array at a plane parallel the reference plane P1. The wells B12 are located over the sensing area Z1. In some embodiments, the wells B12 are not located over the non-sensing area Z2.

In some embodiments, the carrier B1 is made by a semiconductor manufacturing process. The carrier B1 is integrated with the light-guiding structure 2. In some embodiments, the carrying body B11 is made from transparent material, such as glass. Each of the wells B12 is configured to receive the specimen B2. In some embodiments, the specimen B2 includes blood, biological tissue, or DNA fragmentations.

The light-guiding structure 2 is configured to transmit and guide the excitation beam L1 to the specimen B2 by passing through the carrying body B11. The light-guiding structure 2 is a plate structure parallel to the image sensor 1, the carrier B1, and the reference plane P1. In some embodiments, the light-guiding structure 2 is made by a semiconductor manufacturing process. The light-guiding structure 2 is integrated with the image sensor 1.

The light-guiding structure 2 includes a bottom layer 21, a central guiding portion 22, a reflection layer 23, first guiding portions 24, and a top layer 25. Each of the bottom layer 21, the central guiding portion 22, the reflection layer 23, the first guiding portions 24, and the top layer 25 extends parallel to the reference plane P1.

The bottom layer 21 is disposed on the microlenses 14 and the shielding portion 15 of the image sensor 1. In some embodiments, the bottom layer 21 is directly connected to the microlenses 14 and the shielding portion 15. The bottom layer 21 is located over both of the sensing area Z1 and the non-sensing area Z2. The bottom layer 21 is configured to reflect the excitation beams L1 in the central guiding portion 22 and the first guiding portions 24.

The central guiding portion 22 is disposed on the bottom layer 21, and located over the sensing area Z1. In some embodiments, the central guiding portion 22 is not located over the non-sensing area Z2. The central guiding portion 22 is configured to transmit and guide the excitation beam L1 from the first guiding portions 24 to the specimen B2

The reflection layer 23 is disposed on the bottom layer 21 of the image sensor 1, and connected to and surrounding the central guiding portion 22. The reflection layer 23 is located over the non-sensing area Z2. In some embodiments, the reflection layer 23 is not located over the sensing area Z1. The reflection layer 23 is configured to reflect the excitation beam L1 to the first guiding portions 24 and the central guiding portion 22.

The reflection layer 23 includes a number of channels 231 located over the non-sensing area Z2. The channels 231 extend from the side surfaces S1 to the central guiding portion 22. In the embodiment, the first guiding portions 24 are formed by filing a guiding material, such as a photoresist, into the channel 231. Therefore, first guiding portions 24 are respectively located in the channels 231. The first guiding portions 24 are connected to the central guiding portion 22 and side surfaces S1.

As shown in FIGS. 2 and 3, the first guiding portions 24 are accommodated by the channels 231 to form tunnel structures. In some embodiments, the refractive index of the reflection layer 23 is in a range from about 1.01 to about 1.5. The refractive index of the first guiding portion 24 is in a range from about 1.5 to about 3. The refractive index of the first guiding portion 24 is greater than the refractive index of the reflection layer 23.

In some embodiments, the refractive index of the first guiding portion 24 is greater than the refractive index of the reflection layer 23. Therefore, the excitation beams L1 transmitted in the first guiding portion 24 can be reflected in total internal reflection by the reflection layer 23.

In some embodiments, the reflection layer 23 further includes a number of holes 235 between the channels 231 and located at corners of the reflection layer 23. The reflection of the reflection layer 23 to the excitation beams L1 is improved.

Each of the first guiding portions 24 includes a first end 241 connected to the side surface S1, a second end 242 connected to the central guiding portion 22, and a connection portion 243 connected to and located between the first end 241 and the second end 242.

The first ends 241 at the side surface S1 are connected or adjacent to each other as shown in FIG. 3. The first end 241 is gradually narrowed from the side surface S1 to the connection portion 243. Therefore, most of the excitation beams L1 emitted from the light sources 3 to the side surface S1 of the light-guiding structure 2 can enter into the first guiding portions 24. Moreover, by the shape of the first end 241, the excitation beams L1 is collected to the connection portion 243.

The connection portions 243 at the same side of the image sensor 1 are parallel to each other. The connection portion 243 is configured to guide and collect the excitation beams L1 transmitted toward the central guiding portion 22. The reflection layer 23 is configured to reflect the excitation beam L1 in the first guiding portions 24 by total internal reflection.

In addition, the second ends 242 adjacent to the central guiding portion 22 are connected or adjacent to each other. The second end 242 is gradually narrowed from the central guiding portion 22 to the connection portion 243. By the shape of the second end 242, the excitation beams L1 in the second end 242 is transmitted toward the central guiding portion 22 uniformly.

As shown in FIG. 2, the height H1 of the bottom surface 221 of the central guiding portion 22 relative to the image sensor 1 is greater than the height H3 of the bottom surface 233 of the first guiding portion 24 relative to the image sensor 1. Moreover, the first guiding portion 24 further includes an inclined surface 234 connected to the bottom surface 221 and the bottom surface 233.

In some embodiments, the reflection layer 23 further includes a number of scattering bumps 232 disposed on bottom surfaces 233 of the channels 231. As shown in FIG. 2, the scattering bumps 232 improve the reflection of the excitation beam L1 and the transmission of the excitation beams L1 into the central guiding portion 22.

The top layer 25 is disposed on the central guiding portion 22. The top layer 25 is located over the sensing area Z1. In some embodiments, the top layer 25 is not located over the non-sensing area Z2. The top layer 25 includes a grid portion 251 and a number of second guiding portions 252.

The grid portion 251 and the second guiding portions 252 are disposed on the central guiding portion 22. The grid portion 251 and the second guiding portions 252 are arranged at a plane parallel the reference plane P1. As shown in FIGS. 2 and 3, the grid portion 251 is surrounding the second guiding portions 252, and the second guiding portions 252 are arranged in a guiding array. Each of the wells B12 is located over one of the second guiding portions 252.

The grid portion 251 is configured to reflect the excitation beam L1 in the central guiding portion 22. The excitation beam L1 in the central guiding portion 22 is transmitted to the specimens B2 via the second guiding portions 252.

The central guiding portion 22, the first guiding portions 24, and second guiding portions 252 are transparent. In some embodiments, the refractive index of the bottom layer 21 is in a range from about 1.01 to about 1.5. The refractive index of the central guiding portion 22 is in a range from about 1.5 to about 3. The refractive index of the second guiding portion 252 is in a range from about 1.5 to about 3. The refractive index of the grid portion 251 is in a range from about 1.01 to about 1.5.

In some embodiments, the refractive indexes of the central guiding portion 22 and the second guiding portion 252 are greater than the refractive indexes of the bottom layer 21 and the grid portion 251.

In some embodiments, the refractive index of the central guiding portion 22 is equal to the refractive index of the second guiding portion 252. The central guiding portion 22 and the second guiding portion 252 are made from the same material and formed as a single piece.

In some embodiments, the refractive index of the grid portion 251 is equal to the refractive index of the bottom layer 21. The grid portion 251 and the bottom layer 21 are made from the same material and formed as a single piece.

In some embodiments, the refractive index of the central guiding portion 22 is equal to the refractive index of the first guiding portion 24. The central guiding portion 22 and the first guiding portion 24 are made from the same material and formed as a single piece.

In some embodiments, the refractive index of the reflection layer 23 is equal to the refractive index of the grid portion 251. The reflection layer 23 and the grid portion 251 are made from the same material and formed as a single piece.

In this embodiment, the central guiding portion 22 is located between the bottom layer 21 and the top layer 25. The grid portion 251 is configured to reflect the excitation beam L1 in the central guiding portion 22 by total internal reflection, and the bottom layer 21 is configured to reflect a portion of the excitation beam L1 in the central guiding portion 22 by total internal reflection. Therefore, the excitation beam L1 can be transmitted along the central guiding portion 22.

In addition, the microlens 14 includes a refractive index in a range from about 1.4 to about 2.3. The excitation beam L1 directly transmitted to the microlens 14 or reflected to the microlens 14 by the grid portion 251 is reflected toward the wells B12 via the second guiding portions 252 by the microlenses 14.

As shown in FIGS. 2 and 3, the light sources 3 are adjacent to the side surfaces S1 of the first guiding portions 24, and configured to emit the excitation beam L1 into the central guiding portion 22 via the first guiding portions 24. By the structure of the reflection layer 23 and the first guiding portions 24, the light emitting efficiency of the light sources 3 is improved, and the excitation beams L1 in the first guiding portions 24 transmitted toward the central guiding portion 22 are uniform.

When the excitation beam L1 is transmitted in the central guiding portion 22, a portion of the excitation beam L1 is transmitted along central guiding portion 22 by total internal reflection. Moreover, a portion of the excitation beam L1 is transmitted to the microlenses 14 and is reflected by the microlenses 14. Therefore, a portion of the excitation beam L1 reflected by the microlenses 14 is transmitted to the specimens B2 via the second guiding portions 252 and the carrying body B11.

The specimen B2 emits induced beam L2 when the specimen B2 is irradiated by the excitation beam L1. A portion of the induced beam L2 is blocked by the grid portion 251. A portion of the induced beam L2 is transmitted to the image sensor 1 via the second guiding portions 252 and the central guiding portion 22 in sequence. When the induced beams L2 fall on the image sensor 1, the induced beams L2 are transmitted to the sensing layer 11 via the microlenses 14 and the filter units 13 in sequence.

The induced beams L2 are focused by the microlenses 14. Each of the filter units 13 allows a predetermined range of wavelengths of the induced beams L2 to pass. Each of the sensing units 112 generates a detection signal according to the induced beam L2 falling thereon.

For example, as shown in FIG. 2, if the induced beam L2 is a red beam, the induced beam L2 can pass through the red filter unit 13a but is blocked by the yellow filter unit 13b. Therefore, the sensing unit 112 corresponding to the red filter unit 13a generates a detection signal, but the sensing unit 112 corresponding to the yellow filter unit 13b does not generate a detection signal. Since the sensing units 112 corresponding to the red filter unit 13a and the sensing units 112 corresponding to the yellow filter unit 13b correspond to the specimen B2a and the wells B12a, the color of the induced beam L2 generated by the specimen B2a can be determined.

Since the detection device 100 is made by a semiconductor manufacturing process, the size of the detection device 100 is small, and the weight of the detection device 100 is light. In some embodiments, the width or the length of the detection device 100 is in a range of about 6.35 mm to about 12.7 mm, and the thickness of the detection device 100 is in a range of about 3 um to about 4.5 um. Therefore, the detection device 100 is portable. Moreover, the manufacturing cost of the detection device 100 is cheaper than the conventional biochip detection device having a large amount of optical elements.

In addition, the image sensor 1 integrates with the light-guiding structure 2, and the image sensor 1 senses the induced beams L2 generated by the specimens B2 at the same time. Therefore, the time required for detection of the specimens B2 of the detection device 100 is decreased.

Figure 4:
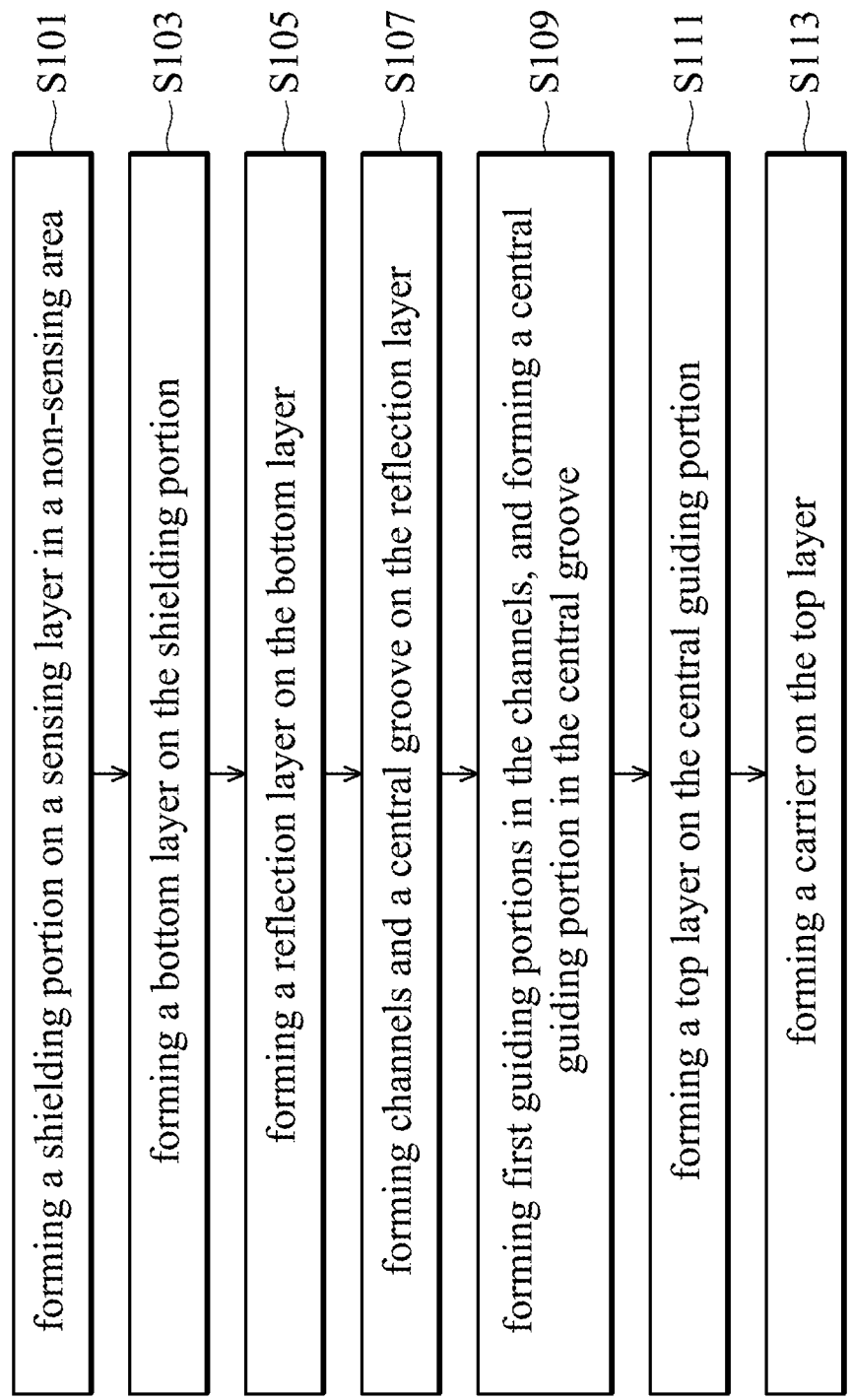
FIG. 4 is a flow chart of a manufacturing method of the detection device in accordance with some embodiments of the present disclosure.

FIG. 4 is a flow chart of a manufacturing method of the detection device 100 in accordance with some embodiments of the present disclosure. FIGS. 5A to 5H are schematic views of the manufacturing method of the detection device 100 during intermediate stages in accordance with some embodiments of the disclosure.

Figure 5A:
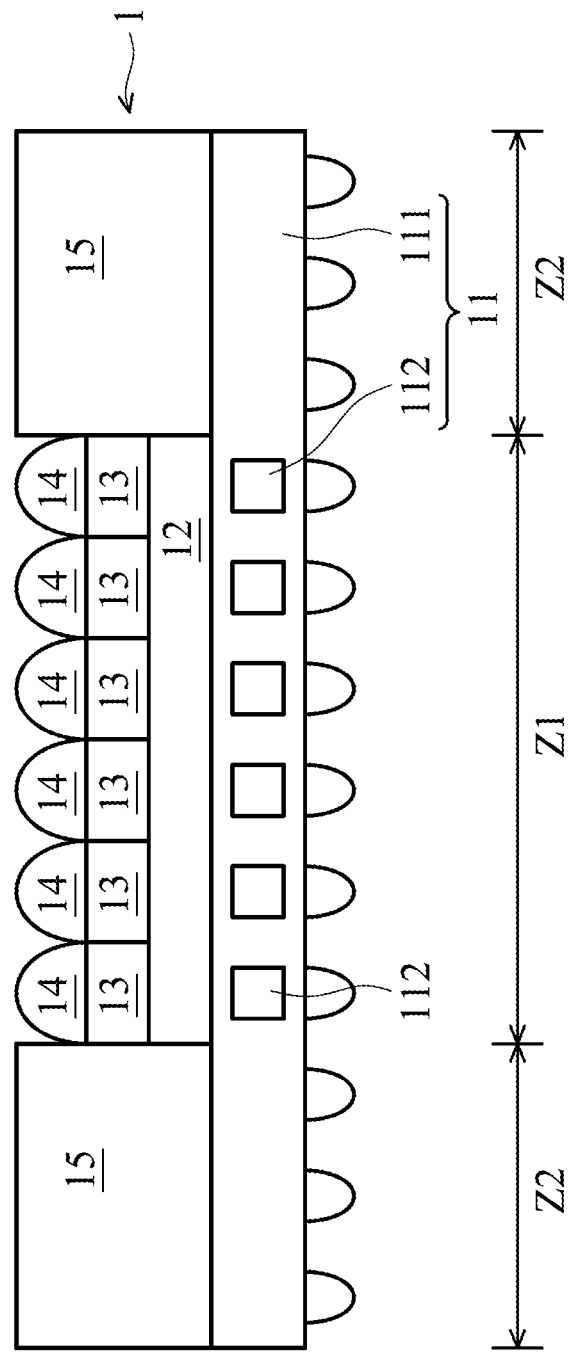
FIGS. 5A to 5F are schematic views of the manufacturing method of the detection device during intermediate stages in accordance with some embodiments of the disclosure.

In step S101, as shown in FIG. 5A, the cutting layer 12 is formed on the sensing layer 11 over the sensing area Z1, the filter units 13 are formed on the cutting layer 12, and the microlenses 14 are formed on the filter units 13 in sequence. Afterward, the shielding portion 15 is formed on the sensing layer 11 over the non-sensing area Z2. In some embodiments, the shielding portion 15 is a photoresist. The color of the shielding portion 15 is black.

Figure 5B:
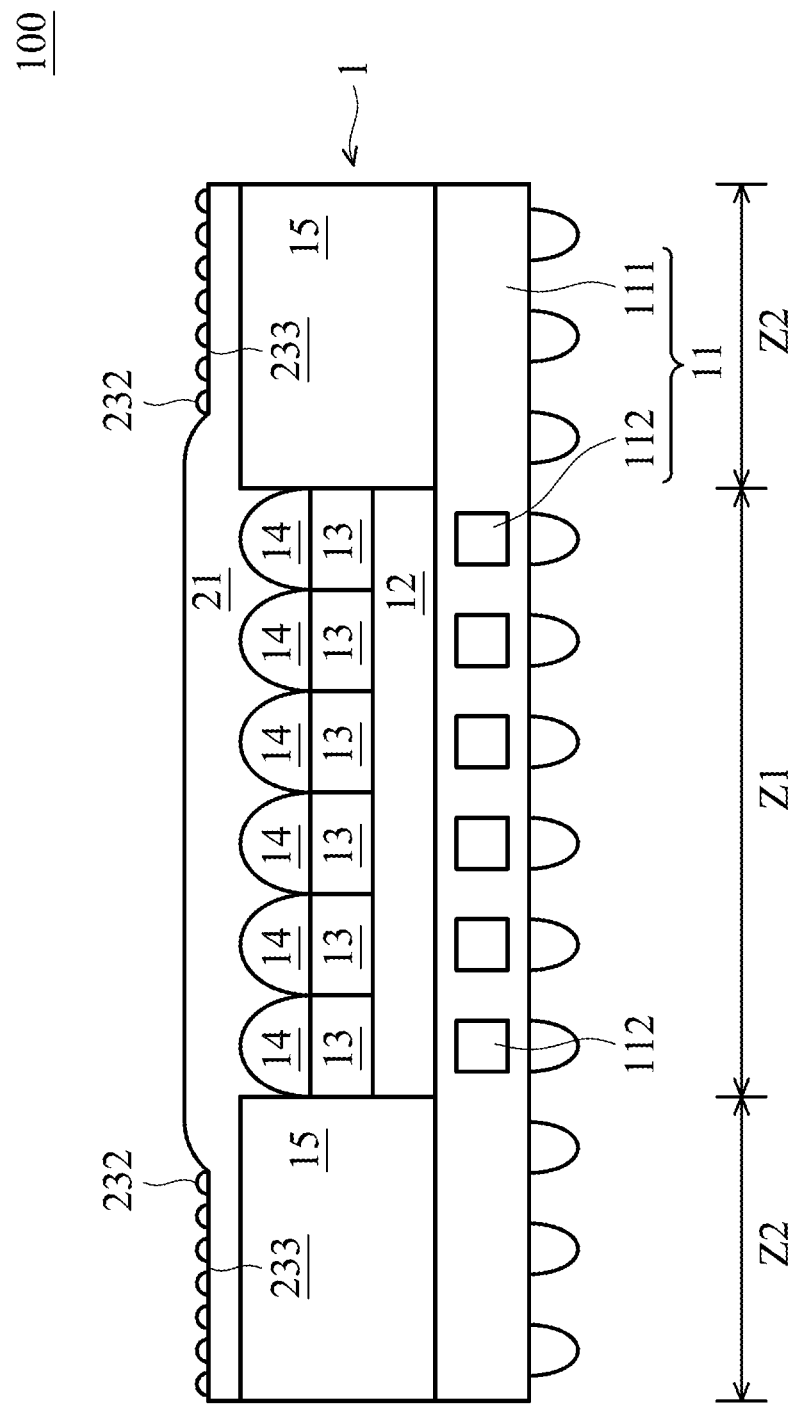
Figure 5C:
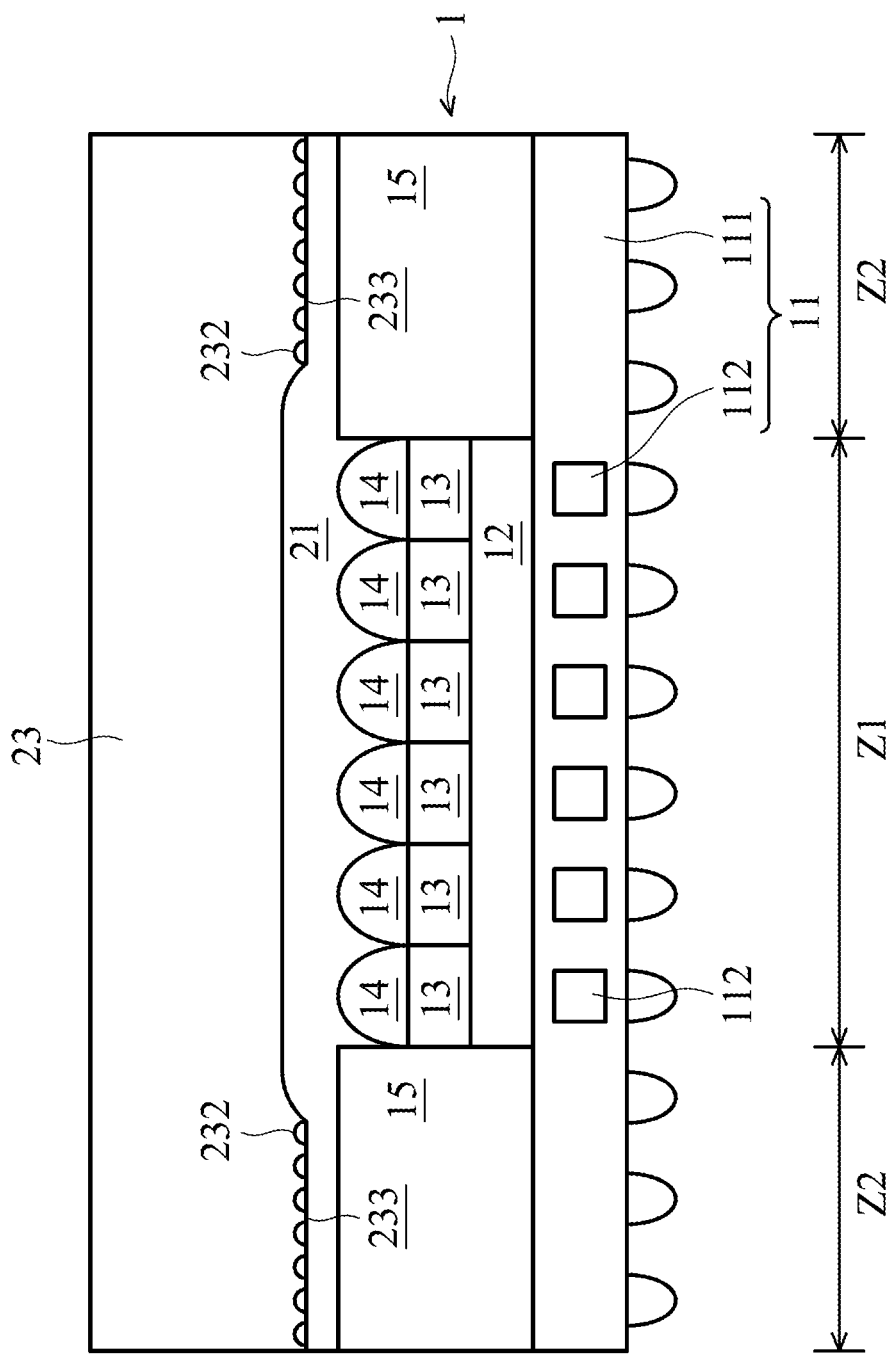

In step S103, as shown in FIG. 5B, the bottom layer 21 is formed on the shielding portion 15 and the microlenses 14. In step S105, as shown in FIG. 5C, the reflection layer 23 is formed on the bottom layer 21.

Figure 5D:
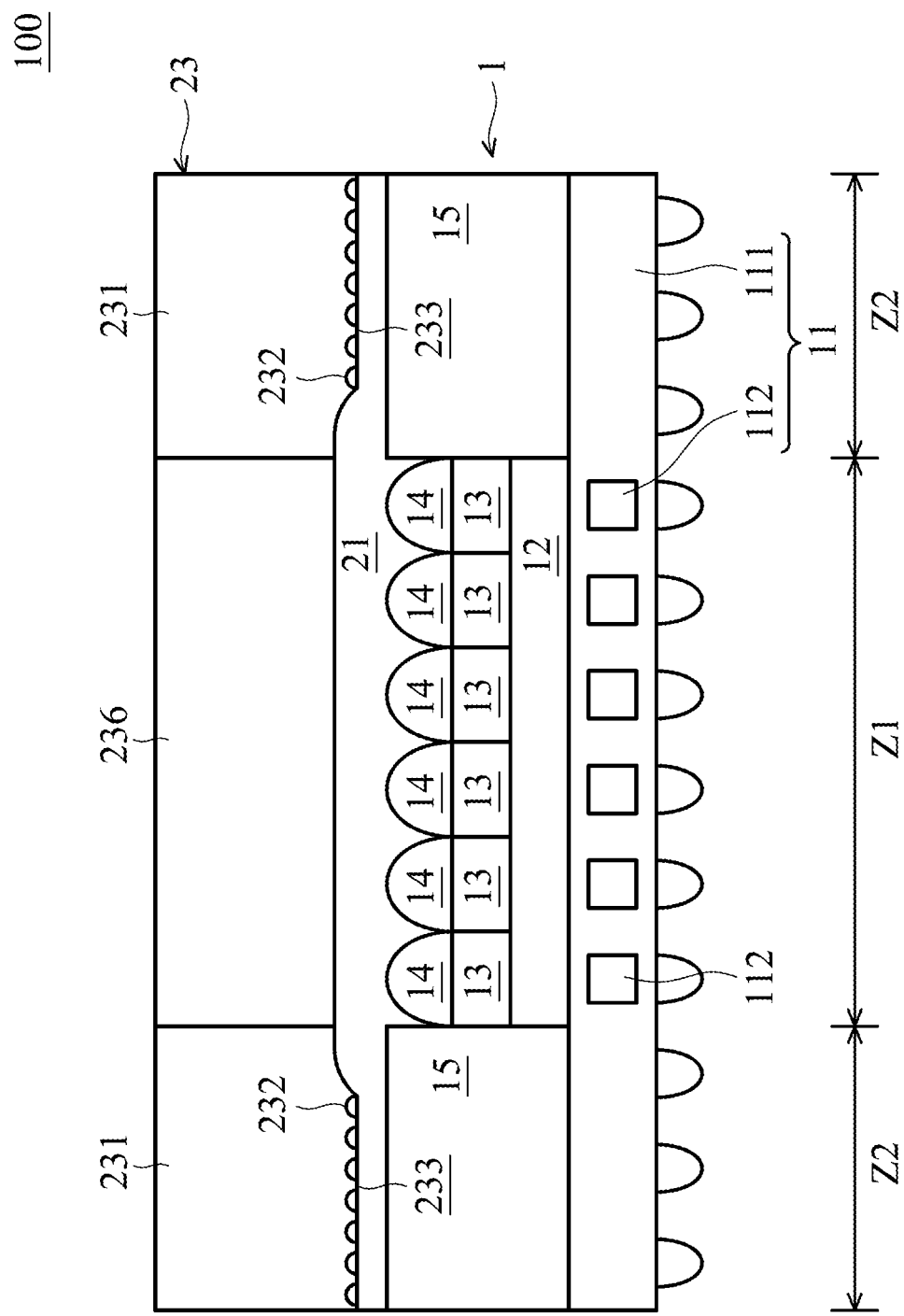

In step S107, as shown in FIG. 5D, the channels 231 are formed on the reflection layer 23 over the non-sensing area Z2, and a central groove 236 is formed on the reflection layer 23 over the sensing area Z1. The channels 231 are respectively connected to the central groove 236. In some embodiments, the channels 231 and the central groove 236 are formed by an etching process.

Figure 5E:
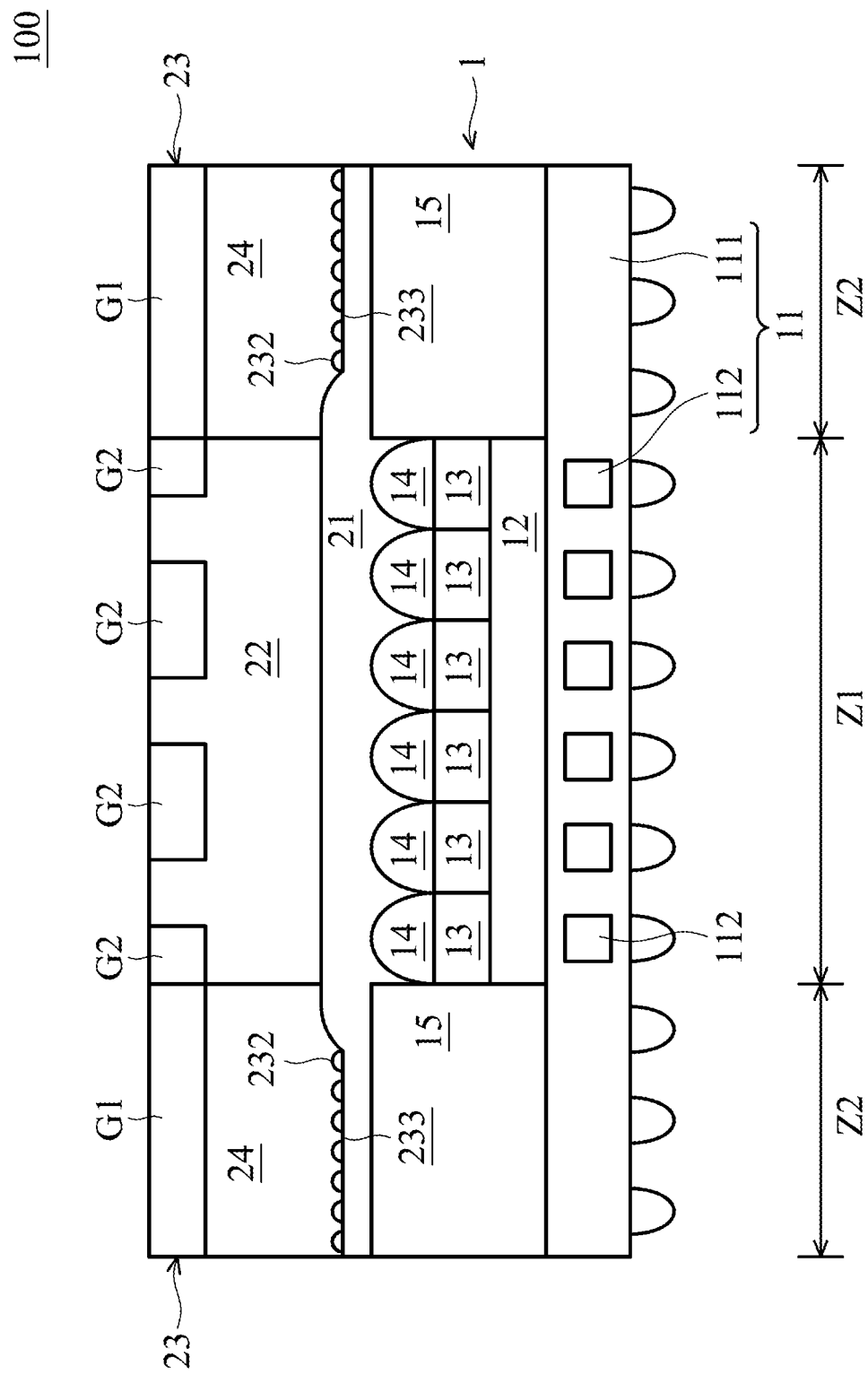

In step S109, as shown in FIG. 5D, a guiding material is filled into the channels 231 and the central groove 236. In some embodiments, the guiding material is a photoresist. As shown in FIG. 5E, the guiding material located over the non-sensing area Z2 forms the first guiding portions 24. The guiding material located over the sensing area Z1 forms the central guiding portion 22.

Afterwards, filling grooves G1 are formed by etching top portions of the first guiding portions 24, and filling grooves G2 are formed by etching the top portion of the central guiding portion 22.

Figure 5F:
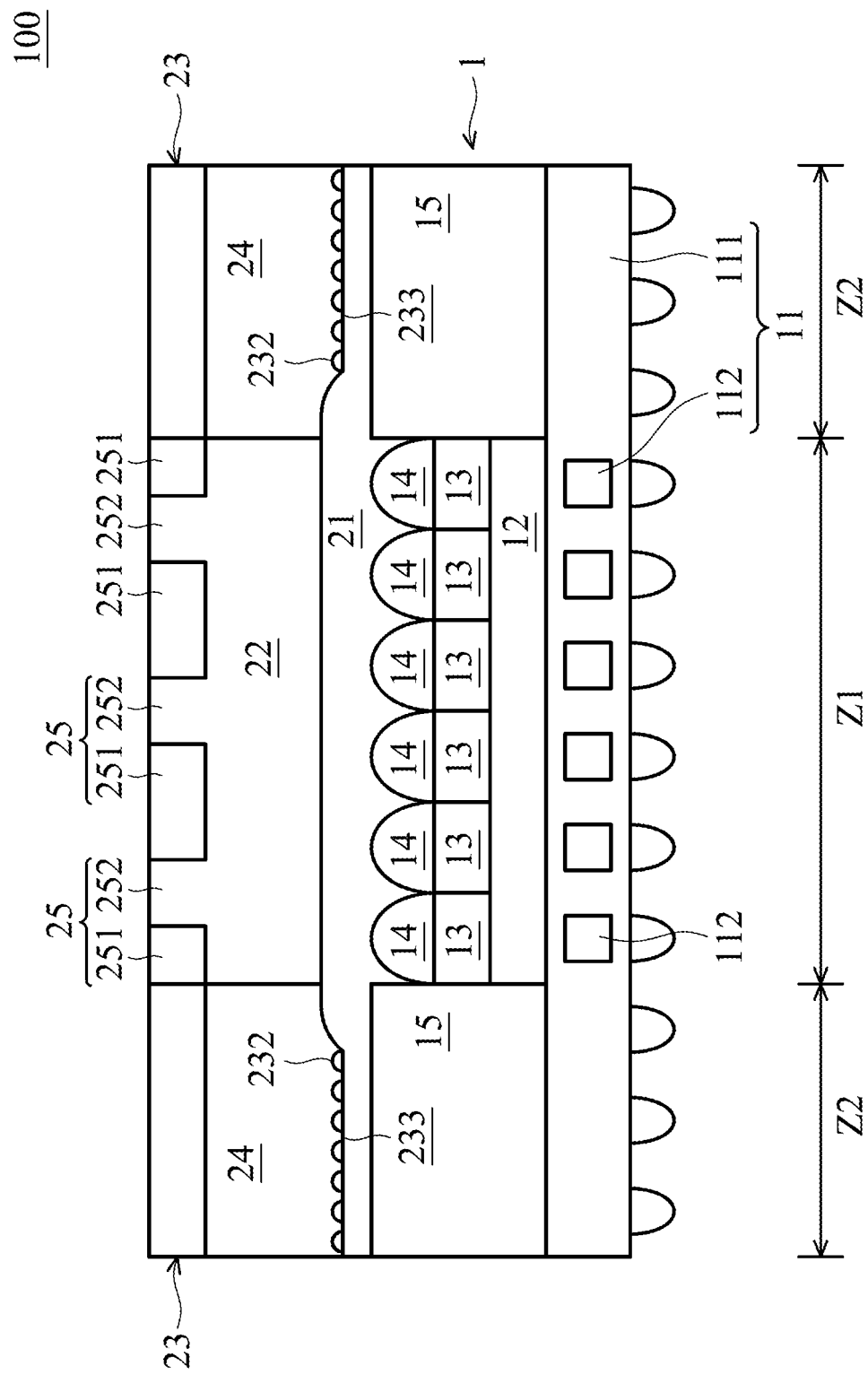

In step S111, as shown in FIG. 5F, a reflecting material is filled into the filling grooves G1 and G2. In some embodiments, the reflecting material is a photoresist. The reflecting material in the filling grooves G1 is formed as a part of the reflection layer 23.

The reflecting material in the filling grooves G2 is formed to the grid portions 251, and the top of the central guiding portion 22 are formed as the second guiding portions 252. Therefore, the top layer 25 is formed by the grid portions 251 and the second guiding portions 252. In step S113, as shown in FIG. 2, the carrier B1 is formed on the top layer 25.

By the manufacturing method of the detection device 100, the image sensor 1, the light-guiding structure 2, and/or the carrier B1 can be made by a semiconductor manufacturing process. The manufacture of the detection device 100 is simplified, and the size of the detection device 100 can be reduced.

Figure 6A:
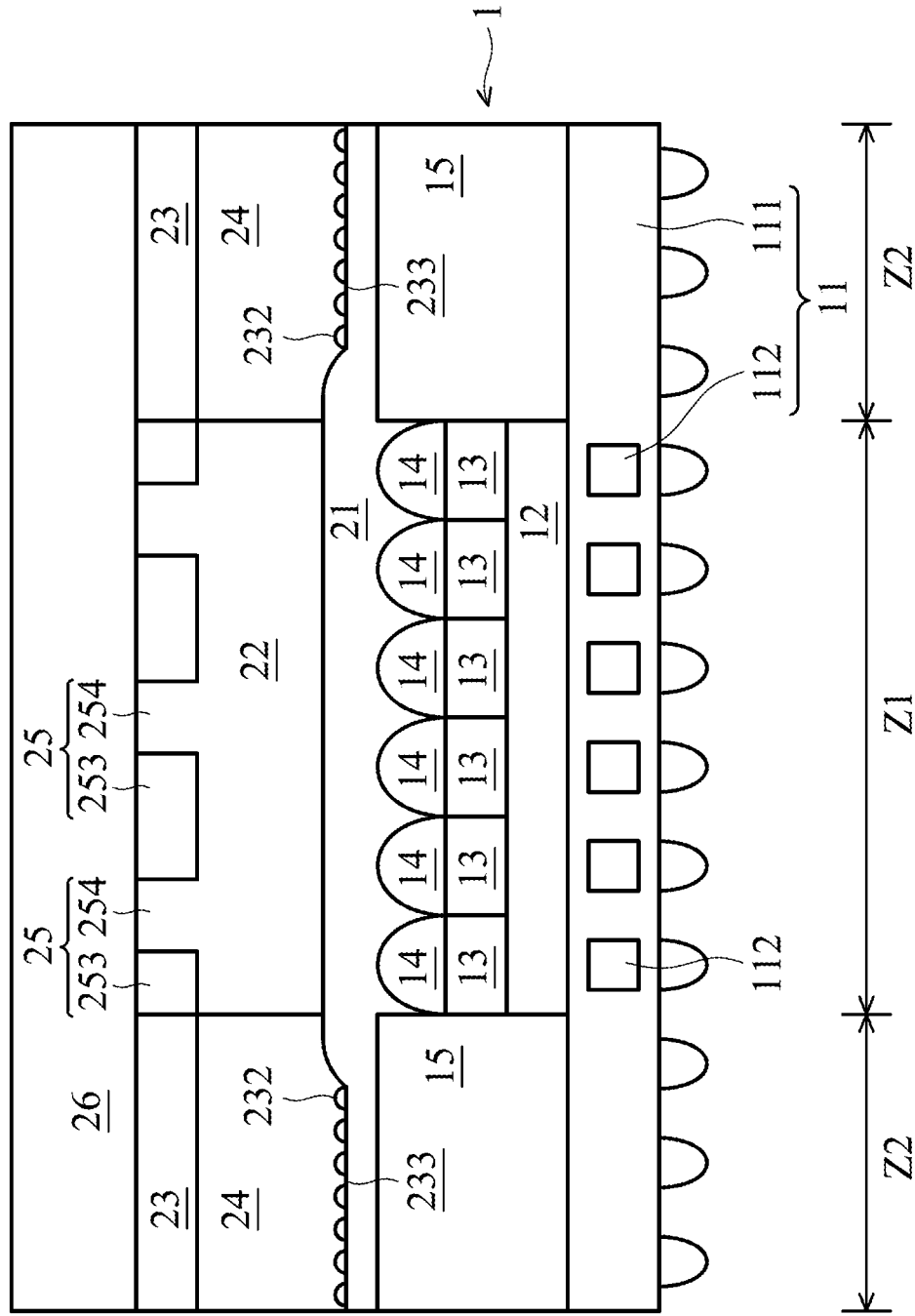
FIGS. 6A and 6B are schematic views of the manufacturing method of the detection device during intermediate stages in accordance with some embodiments of the disclosure.
Figure 6B:
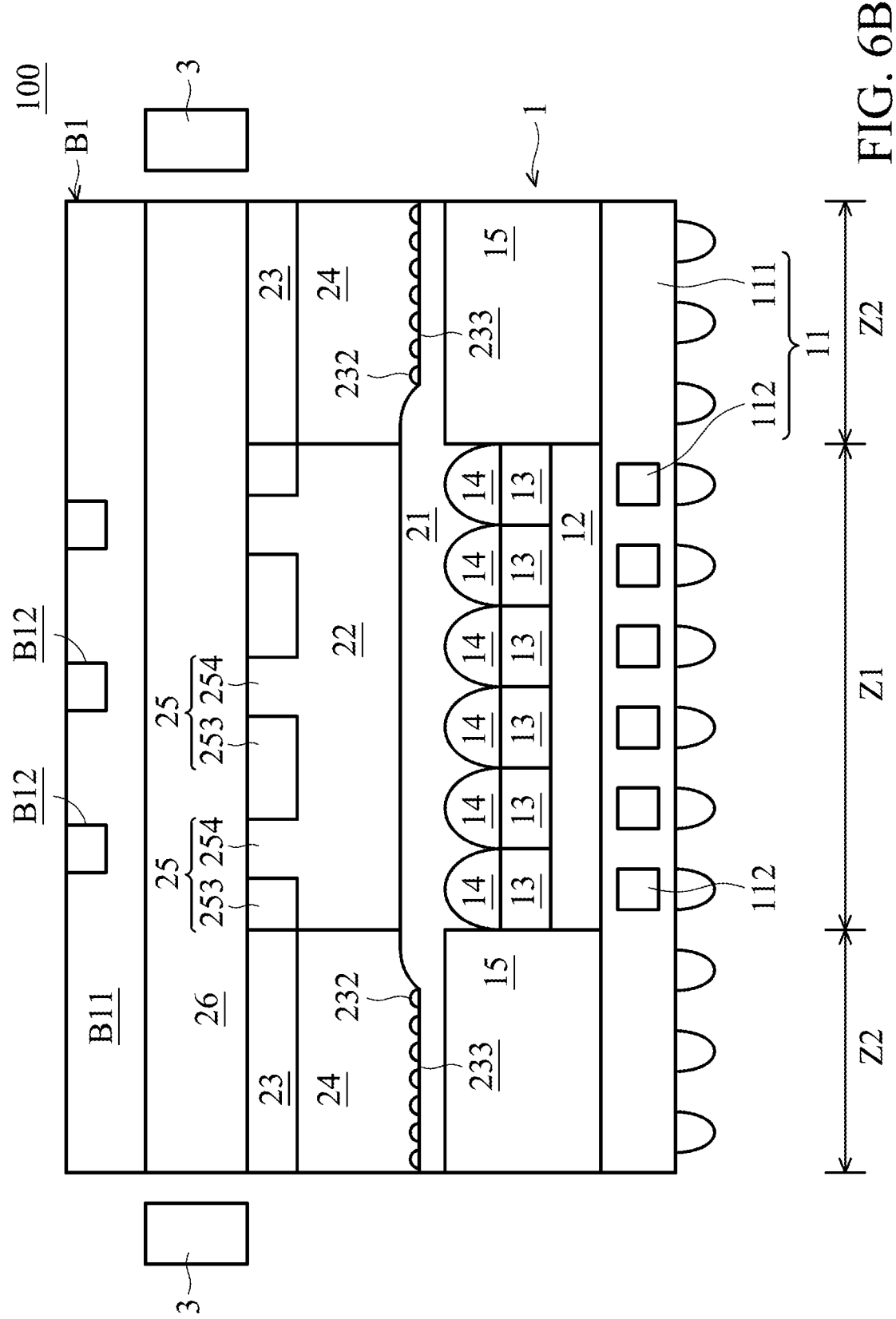

FIGS. 6A and 6B are schematic views of the manufacturing method of the detection device 100 during intermediate stages in accordance with some embodiments of the disclosure. As shown in FIGS. 5E and 6A, in the step S109, the filling grooves G2 are linear structures and parallel to each other. In step S111, the reflecting material is filled into the filling grooves G2 to form first grating portions 253, and the top of the central guiding portion 22 are formed as second grating portions 254. The top layer 25 is formed by the first grating portions 253 and the second grating portions 254.

In some embodiments, the first grating portions 253 and the second grating portions 254 are alternately arranged. The first grating portions 253 and the second grating portions 254 are liner structures and are parallel to each other.

After the first grating portions 253 and the second grating portions 254 are formed, a transmitting layer 26 is formed on the reflection layer 23 and the top layer 25. In some embodiments, the transmitting layer 26 is made of the reflecting material. The first grating portions 253 and the transmitting layer 26 are formed at the same time.

As shown in FIG. 6B, in the step S113, the carrier B1 is formed on the transmitting layer 26, and the light source 3 is adjacent to the transmitting layer 26. The light source 3 emits the excitation beams into the transmitting layer 26.

In conclusion, since the detection device is integrated with the image sensor and the light-guiding structure, the size and the weight of the detection device are greatly decreased, and the manufacturing cost of the detection device is cheap. By the light-guiding structure, the light emitting efficiency of the light sources is improved. Moreover, the specimens on the carrier can be detected by the image sensor at the same time, and the thus the time required for detection of the specimens is decreased.

While the invention has been described by way of example and in terms of preferred embodiment, it is to be understood that the invention is not limited thereto. On the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A detection device for specimens, comprising:
   an image sensor, comprising a sensing area and a non-sensing area encircling the sensing area, wherein the image sensor includes a plurality of sensing units located in the sensing area, and the plurality of sensing units are absent in the non-sensing area;
   a light-guiding structure, disposed on the image sensor, comprising:
      a central guiding portion, located over the sensing area of the image sensor;
      a reflection layer, connected to and encircling the central guiding portion, wherein the reflection layer is located over the non-sensing area of the image sensor; and
      a plurality of first guiding portions located in the reflection layer and connected to the central guiding portion and a side surface of the light-guiding structure; and
   a carrier, disposed on the light-guiding structure, having a plurality of wells arranged in an arrangement array located over the sensing area of the image sensor, wherein each of the wells is configured to receive a specimen;
   wherein the refractive index of the central guiding portion is equal to the refractive index of the first guiding portion; and
   wherein a height of a first bottom surface of the central guiding portion relative to the image sensor is greater than a height of a second bottom surface of each of the first guiding portions relative to the image sensor.

2. The detection device for specimens as claimed in claim 1, wherein the reflection layer further comprises a plurality of scattering bumps disposed on a bottom surface contacting the plurality of first guiding portions.

3. The detection device for specimens as claimed in claim 1, wherein each of the first guiding portions further comprises an inclined surface connected to the first bottom surface and the second bottom surface.

4. The detection device for specimens as claimed in claim 1, wherein each of the first guiding portions comprising a first end connected to the side surface, a second end connected to the central guiding portion, and a connection portion located between the first end and the second end, wherein the first end is gradually narrowed from the side surface to the connection portion.

5. The detection device for specimens as claimed in claim 4, wherein the second end is gradually narrowed from the central guiding portion to the connection portion.

6. The detection device for specimens as claimed in claim 4, wherein the connection portion of one of the first guiding portions is parallel to the connection portion of the other of the first guiding portions.

7. The detection device for specimens as claimed in claim 1, wherein the reflection layer further comprises a plurality of holes located at corners of the reflection layer.

8. The detection device for specimens as claimed in claim 1, wherein a refractive index of each of the first guiding portions is greater than a refractive index of the reflection layer.

9. The detection device for specimens as claimed in claim 1, further comprising a light source adjacent to the side surface of the central guiding portion, configured to emit an excitation beam into the central guiding portion via the first guiding portions.

10. The detection device for specimens as claimed in claim 9, wherein the specimens emit induced beams when the specimens are irradiated by the excitation beam, and the induced beams are transmitted to the image sensor via the central guiding portion.

11. The detection device for specimens as claimed in claim 9, wherein the light-guiding structure further comprises a plurality of second guiding portions disposed on the central guiding portion.

12. The detection device for specimens as claimed in claim 11, wherein the excitation beam is transmitted to the specimens via the second guiding portions.

13. The detection device for specimens as claimed in claim 11, wherein the light-guiding structure further comprises a central reflection portion, surrounding the second guiding portions, disposed on the central guiding portion and located over the sensing area, wherein the central reflection portion is configured to reflect the excitation beam in the central guiding portion.

14. The detection device for specimens as claimed in claim 10, wherein the light-guiding structure further comprises a bottom layer located over the sensing area, wherein the bottom layer is configured to reflect the excitation beam in the central guiding portion.

15. The detection device for specimens as claimed in claim 10, wherein the image sensor comprises:
- a sensing layer;
- a plurality of filter units, located in the area;
- a plurality of microlenses, disposed on the filter units; and
- a shielding portion, located in the non-sensing area, around the filter units and the microlenses,
- wherein the light-guiding structure is disposed on the microlenses, and the microlenses are configured to reflect the excitation beam toward the wells.

16. The detection device for specimens as claimed in claim 15, wherein the induced beams are transmitted to the sensing layer via the microlenses and the filter units in sequence.

* * * * *